(12) United States Patent
Ogisu et al.

(10) Patent No.: US 7,405,391 B2
(45) Date of Patent: Jul. 29, 2008

(54) MODULAR SENSOR FOR DAMAGE DETECTION, MANUFACTURING METHOD, AND STRUCTURAL COMPOSITE MATERIAL

(75) Inventors: Toshimichi Ogisu, Tokyo (JP); Seiji Kojima, Hitachi (JP)

(73) Assignee: Fuji Jukogyo Kabushiki Kaisha, Tokyo (JP)

( * ) Notice: Subject to any disclaimer, the term of this patent is extended or adjusted under 35 U.S.C. 154(b) by 76 days.

(21) Appl. No.: 11/304,262

(22) Filed: Dec. 14, 2005

(65) Prior Publication Data
US 2008/0156971 A1 Jul. 3, 2008

(30) Foreign Application Priority Data
Dec. 15, 2004 (JP) ............................. 2004-362867

(51) Int. Cl.
*G01J 1/04* (2006.01)
*G02B 6/00* (2006.01)
*G02B 6/38* (2006.01)

(52) U.S. Cl. ............................. 250/227.14; 250/227.16; 385/12; 385/72

(58) Field of Classification Search ............ 250/227.11, 250/216, 225, 227.23, 227.13–227.17; 385/12, 385/13, 37, 55, 70, 58, 60, 61, 63, 66, 72, 385/78, 85, 88; 398/108, 161; 356/32, 34; 73/800
See application file for complete search history.

(56) References Cited

U.S. PATENT DOCUMENTS

| | | | |
|---|---|---|---|
| 5,493,390 A | 2/1996 | Varasi | |
| 6,490,931 B1 * | 12/2002 | Fernald et al. | 73/705 |
| 6,586,722 B1 * | 7/2003 | Kenny et al. | 250/227.16 |
| 6,740,866 B1 * | 5/2004 | Bohnert et al. | 250/227.14 |
| 2007/0006663 A1 * | 1/2007 | Zerwekh et al. | 73/800 |

FOREIGN PATENT DOCUMENTS

| | | |
|---|---|---|
| EP | 0640824 A | 3/1995 |
| JP | 2002-162211 | 10/2002 |
| JP | 2003-222571 | 8/2003 |
| JP | 2004-038093 | 5/2004 |
| WO | WO 03/076887 | 9/2003 |

OTHER PUBLICATIONS

Guemes, JA, et al.: "Experimental Analysis of Buckling In Aircraft Skin Panels By Fiber Optic Sensors", Smart Material and Structure IOP Publishing UK, vol. 10, No. 3, Jun. 2001; pp. 490-496.

Foote, PD et al.; Optical Sensor for Aerospace Structure Montoring IEE Colloquium; Optical Techniques for Structure Monitoring: Digest No. 1995/087; 1995; [ages 2/1-2/6.

(Continued)

Primary Examiner—Georgia Y. Epps
Assistant Examiner—Don Williams
(74) Attorney, Agent, or Firm—Smith, Gambrell & Russell

(57) ABSTRACT

A modular sensor for damage detection with an optical fiber (FBG sensor) to detect a damage of a composite material, having a high level of visibility and manageability, and its manufacturing method is described. A structural composite material embedded with this modular sensor for damage detection is also described.

25 Claims, 8 Drawing Sheets

OTHER PUBLICATIONS

Tsutsui H., et al; detrction of Impact Damage of Stiffened Composite Panels Using Embedded Small-Diameter Optical Fibers; Smart Material and Structures IOP Publishing UK; vol. 13, #6; Sep. 2004; pp. 1284-1290.

Partial European Search Report dated Apr. 19, 2006.

Satori, et al.: "Development of Small-Diameter Optical Fiber Sensors for Damage Detection in Composite Laminates"; Preceedings of the Spie, The International Society for Optical Engineering Spie-Int. Soc. Opt. Eng USA, vol. 3986, 2000, pp. 104-111.

Kabashima et al.: Structural Health Monitoring Using FBG Sensor in Space Enviroment; Preceedings of the Spie, The International Society for Optical Engineering Spie-Int. Soc. Opt. Eng USA, vol. 4332, 2001, pp. 78-87.

European Search Report dated Jul. 18, 2006.

\* cited by examiner

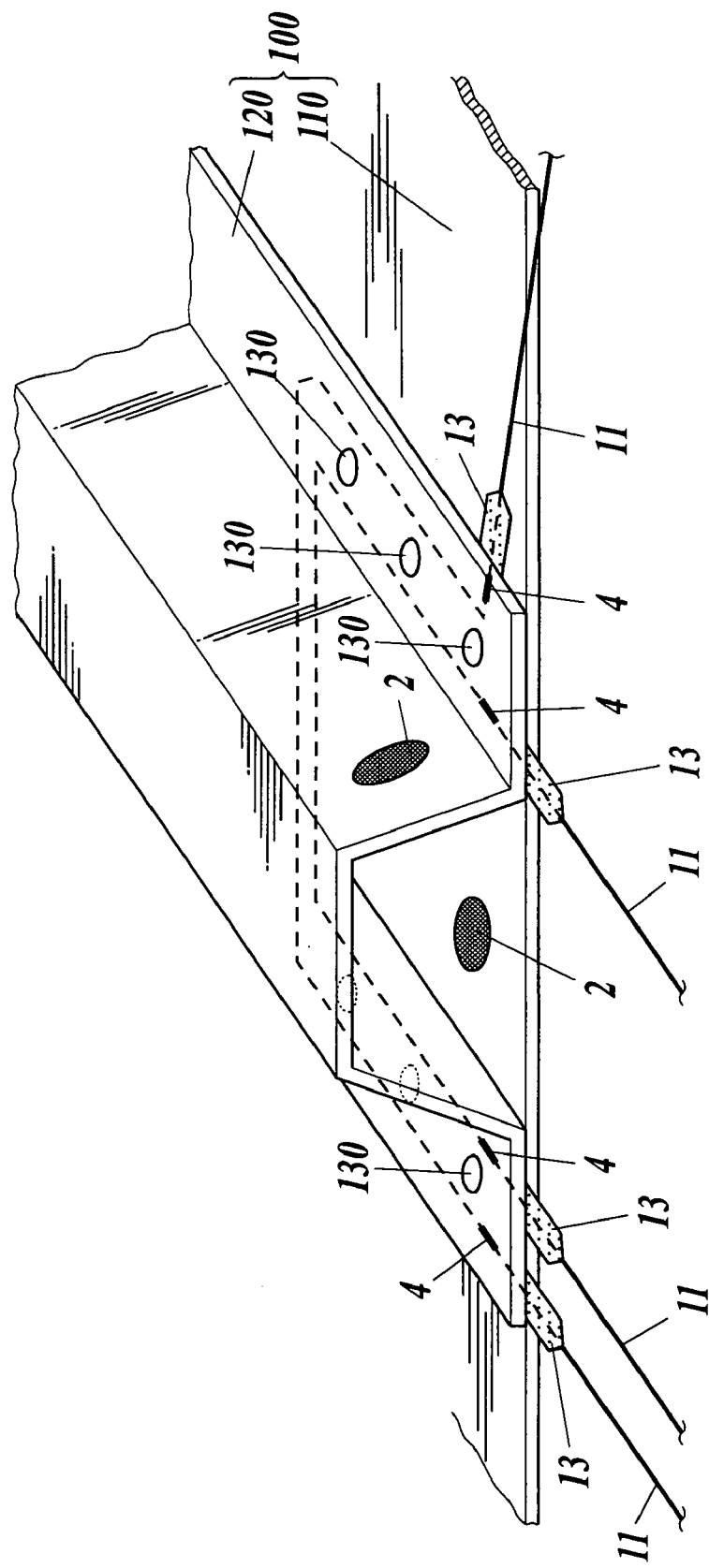

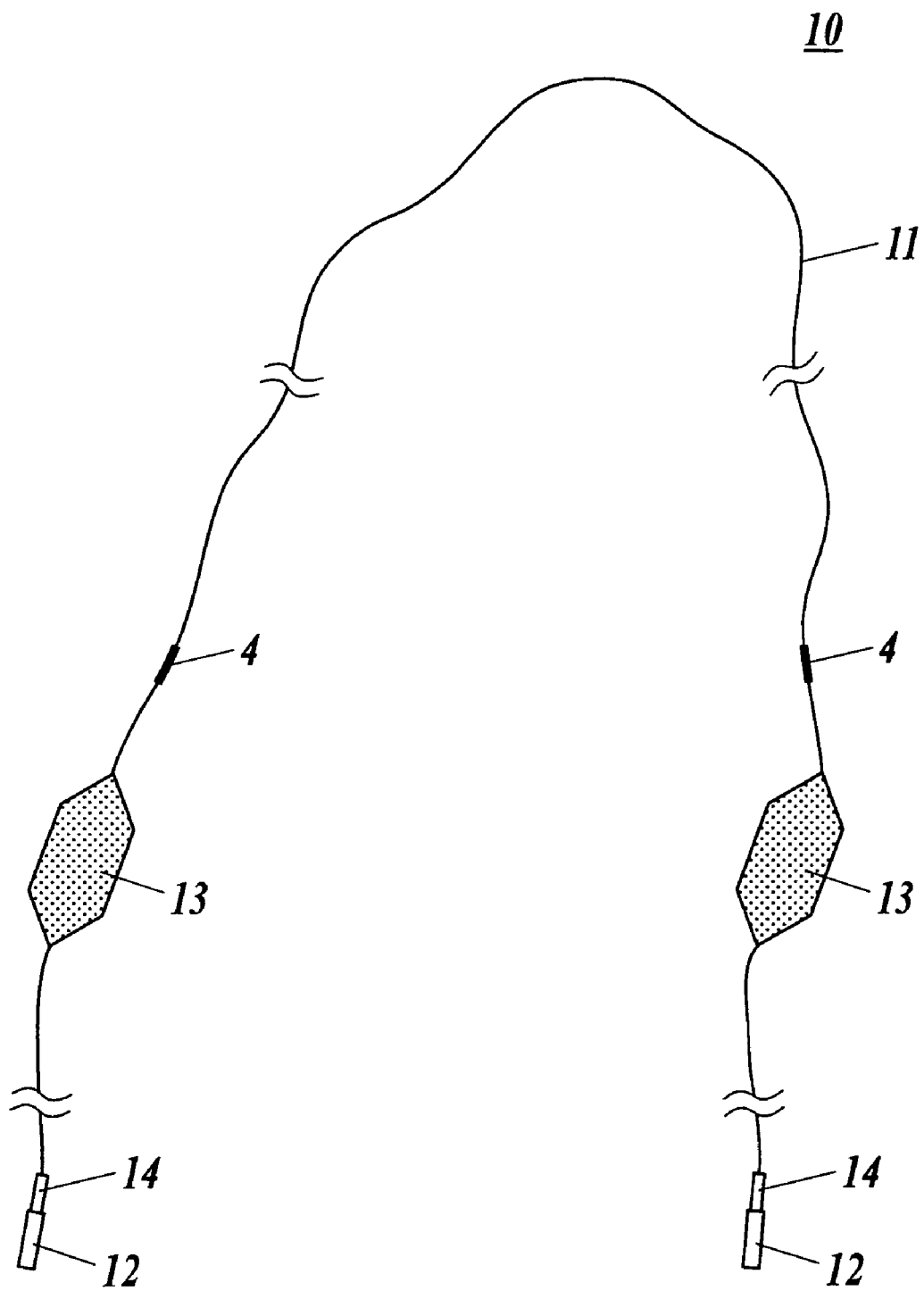

MODULAR SENSOR FOR DAMAGE DETECTION, MANUFACTURING METHOD, AND STRUCTURAL COMPOSITE MATERIAL

BACKGROUND OF THE INVENTION

1. Field of the Invention

The present invention relates to a modular sensor for damage detection, manufacturing method, and structural composite material.

2. Description of the Related Art

Conventionally, fiber reinforced resin composite material (hereinafter called "composite material") which is light and high in strength has been applied to various structural composite materials such as aircraft structures, space equipments, high-rise buildings, public infrastructures, high-speed vehicles, and the like. Since behavior of damage progress of the composite material is unclear compared to that of metal material, "safe life design" has been adopted in case of structuring structural composite material. However, when this design method is adopted, weight of structure becomes heavy, and properties of the composite material (light and high in strength) cannot be taken in advantage fully.

Therefore, in these days, development in technique to detect damage of the composite material is on progress to achieve "damage tolerance design", that can take the properties of the composite material in advantage fully. For example, a technique to embed film-shaped piezo elements and cables sandwiched between polyimide films into the composite material, to detect outputs from the piezo elements which are produced based on vibration applied to the structure, and to detect damage of the composite material based on detected waveforms, has been disclosed (for example, see Patent Document 1: U.S. Pat. No. 6,370,964).

However, since a place where polyimide film used in the technique is embedded is limited, it is difficult to detect damage with high degree of accuracy by embedding the polyimide film where damage occurs frequently. Therefore, recently proposed is to embed an optical fiber provided with FBG (Fiber Bragg Grating) sensor into the composite material, and proposed is a damage detection system to detect damage of the composite material with high degree of accuracy, according to a reflected light property detected by the FBG sensor.

Meanwhile, the optical fiber used in aforementioned damage detection system has a typical wire diameter of 125 μm to 150 μm, which would be approximately same size with a thickness of one prepreg layer constructing the composite material (125 μm to 200 μm). Therefore, the property of the composite material may be decreased. In order to solve this problem, a "thin diameter" optical fiber whose wire diameter is less than or equal to half the thickness of one prepreg layer (approximately 52 μm) has been developed recently.

However, since the thin diameter optical fiber is so thin that managing with the optical fiber is difficult and visibility is disturbed, a problem arose in that it is difficult to embed the optical fiber with thin diameter into the composite material.

SUMMARY OF THE INVENTION

An object of the present invention is to provide a modular sensor for damage detection provided with an optical fiber (FBG sensor) to detect a damage of a composite material, having a high level of visibility and manageability, and its manufacturing method.

Another object of the present invention is to provide a structural composite material embedded with the modular sensor for damage detection.

A first aspect of the present invention is a modular sensor for damage detection, comprising: an optical fiber including an FBG sensor; a connector connected to an end portion of the optical fiber; and a tube to partly cover the optical fiber.

Since the modular sensor for damage detection is structured with end portion of the optical fiber being connected to the connector and part of the optical fiber being covered with tube, the modular sensor for damage detection of the present invention has a high level of visibility compared to optical fiber alone, achieving benefit of significant manageability. In addition, by placing the tube at the end portion of the composite material when embedding the modular sensor for damage detection of the present invention into the composite material, breakage of the optical fiber can be prevented by inhibiting stress concentration to the optical fiber at a portion where the optical fiber is drawn out.

Preferably, the tube of the modular sensor for damage detection is movable with respect to the optical fiber.

Since the tube structuring the modular sensor for damage detection is movable with respect to the optical fiber, the tube can be moved according to a position of the end portion of the composite material when embedding the modular sensor for damage detection into the composite material. Therefore, the modular sensor for damage detection of the present invention can be applied to composite material of various shapes.

Preferably, the tube of the modular sensor for damage detection is structured with a heat resistant material.

Since the tube of the modular sensor for damage detection is structured with a heat resistance material, hot forming can be performed to the composite material with the tube partly or fully embedded into the composite material.

Preferably, the optical fiber of the modular sensor for damage detection is partly attached to a film.

Since the optical fiber of the modular sensor for damage detection is partly attached to a film, the visibility of the modular sensor for damage detection is even improved and manageability is further improved.

Preferably, the modular sensor for damage detection is provided with a reinforcing tube to reinforce a bonding portion of the optical fiber and the connector.

Since the bonding portion of the optical fiber and the connector is reinforced by the reinforcing tube, breakage of the optical fiber can be suppressed or prevented by preventing stress concentration to the optical fiber when connecting connector to a predetermined adaptor.

A second aspect of the invention is a modular sensor for damage detection, comprising: an optical fiber including an FBG sensor; a connector connected to an end portion of the optical fiber; and a film partly attached to the optical fiber.

Since the modular sensor for damage detection is structured by end portion of the optical fiber being connected to the connector and part of the optical fiber being attached to the film, the modular sensor for damage detection of the present invention has a high level of visibility compared to optical fiber alone, achieving benefit of significant manageability. In addition, by placing the film at the end portion of the composite material when embedding the modular sensor for damage detection of the present invention into the composite material, breakage of the optical fiber can be prevented by inhibiting stress concentration to the optical fiber at a portion where the optical fiber is drawn out.

Preferably, the film of the modular sensor for damage detection is placed in a position with a regular interval from the FBG sensor.

Since the film of the modular sensor for damage detection is placed in a position at a regular interval from the FBG sensor, interval between the FBG sensor and the film is constant, enabling to grasp easily a position of the FBG sensor according to a position of the film. Therefore, the FBG sensor can be placed at precise position, and degree of detection accuracy is improved.

Preferably, the film of the modular sensor for damage detection is structured with a heat resistant material.

Since the film of the modular sensor for damage detection is structured with a heat resistance material, hot forming can be performed to the composite material with the film partly or fully embedded into the composite material.

Preferably, the film of the modular sensor for damage detection is structured so that the film gradually thins down in thickness from center portion towards a boundary with the optical fiber.

Since the film of the modular sensor for damage detection is structured so that the film gradually narrows in width from the center portion towards the boundary with the optical fiber (the film gradually widens up in width from the boundary with the optical fiber towards center portion), the center portion has the highest strength and stiffness. Therefore, by placing the center portion of the film at an end portion of the composite material when embedding the modular sensor for damage detection into the composite material, breakage of the optical fiber can be effectively prevented. In addition, since the film is structured so as to gradually narrow in width from the center portion towards the boundary with the optical fiber, the stiffness decreases gradually from the center portion towards the boundary with the optical fiber. Therefore, flexibility when embedding into the composite material is high.

Preferably, the modular sensor for damage detection is provided with a reinforcing tube to reinforce a bonding portion of the optical fiber and the connector.

Since the bonding portion of the optical fiber and the connector is reinforced by the reinforcing tube, breakage of the optical fiber can be suppressed or prevented by preventing stress concentration to the optical fiber when connecting connector to a predetermined adaptor.

A third aspect of the invention is a manufacturing method to manufacture a modular sensor for damage detection structured with an optical fiber including an FBG sensor; a connector connected to an end portion of the optical fiber; and a tube to partly cover the optical fiber, comprising: a tubular member preparing step to prepare a tubular member, provided with a inner diameter which is slightly larger at a center portion than an outer diameter of the tube and increases smoothly from the center portion to both ends of the tubular member; a tube insertion step to insert one end portion of the tube into the tubular member through one end and restrict a movement of the tube in a diameter direction by placing the end portion in a vicinity of the center portion; an optical fiber insertion step to insert an optical fiber into the other one end portion of the tubular member, and then into the end portion of the tube; a tubular member removal step to remove the tubular member from the tube and the optical fiber; and a connector fixing step to fix the connector to an end portion of the optical fiber.

Since the inner diameter of the both ends is widened for easily inserting the tube or the optical fiber, which can also restrict the movement of the end portion of the tube in the diameter direction, inserting the optical fiber into the tube becomes significantly easy. Therefore, the modular sensor for damage detection can be manufactured in short time efficiently.

A fourth aspect of the invention is a structural composite material wherein an FBG sensor of a modular sensor for damage detection structured with an optical fiber including an FBG sensor; a connector connected to an end portion of the optical fiber; and a tube to partly cover the optical fiber, is embedded.

Since the structural composite material is embedded with the FBG sensor of the modular sensor for damage detection, by adopting damage detection system including this FBG sensor, damage can be detected with high accuracy. Therefore, by adopting the structural composite material of the present invention, "damage tolerance design", which can take the properties of the composite material (light and high in strength) fully in advantage, is achieved, enabling realization of drastic weight saving of a structure (main wing of an aircraft).

Preferably, the FBG sensor is embedded into a stress concentrating portion of the structural composite material, without being covered with the tube, and the tube is partly embedded into and end portion of the structural composite material.

A fifth aspect of the invention is a structural composite material wherein an FBG sensor of a modular sensor for damage detection structured with an optical fiber including an FBG sensor; a connector capable to be connected to an end portion of the optical fiber; and a film partly attached to the optical fiber, is embedded.

Since the structural composite material is embedded with the FBG sensor of the modular sensor for damage detection, by adopting damage detection system including this FBG sensor, damage can be detected with high accuracy. Therefore, by adopting the structural composite material of the present invention, "damage tolerance design", which can take the properties of the composite material (light and high in strength) fully in advantage, is achieved, enabling realization of drastic weight decrease of a structure (main wing of an aircraft).

Preferably, the FBG sensor is embedded into a stress concentrating portion of the structural composite material, and the film is partly embedded into an end portion of the structural composite material.

According to the present invention, by connecting a connector to an end portion of an optical fiber, and connecting a tube and/or a film to a part of the optical fiber, a modular sensor for damage detection, which has a high level of visibility compared to optical fiber alone, achieving significant manageability, can be structured. In addition, since the structural composite material embedded with the FBG sensor of the modular sensor for damage detection of the present invention can detect damage with high accuracy, "damage tolerance design", which can take the properties of the composite material (light and high in strength) fully in advantage, is achieved. Therefore, drastic weight decrease of a structure can be realized.

BRIEF DESCRIPTION OF THE DRAWINGS

The present invention will become more fully understood from the detailed description given hereinbelow and the accompanying drawings which are given by way of illustration only, and thus are not intended as a definition of the limits of the present invention, and wherein;

FIG. 2 is a perspective view showing a composite material for main wing of an aircraft, embedded with the modular sensor for damage detection of the first embodiment of the present invention;

FIG. 3 is a conceptual diagram of the modular sensor for damage detection of the first embodiment of the present invention;

DETAILED DESCRIPTION OF THE PREFERRED EMBODIMENT

Figure 1:
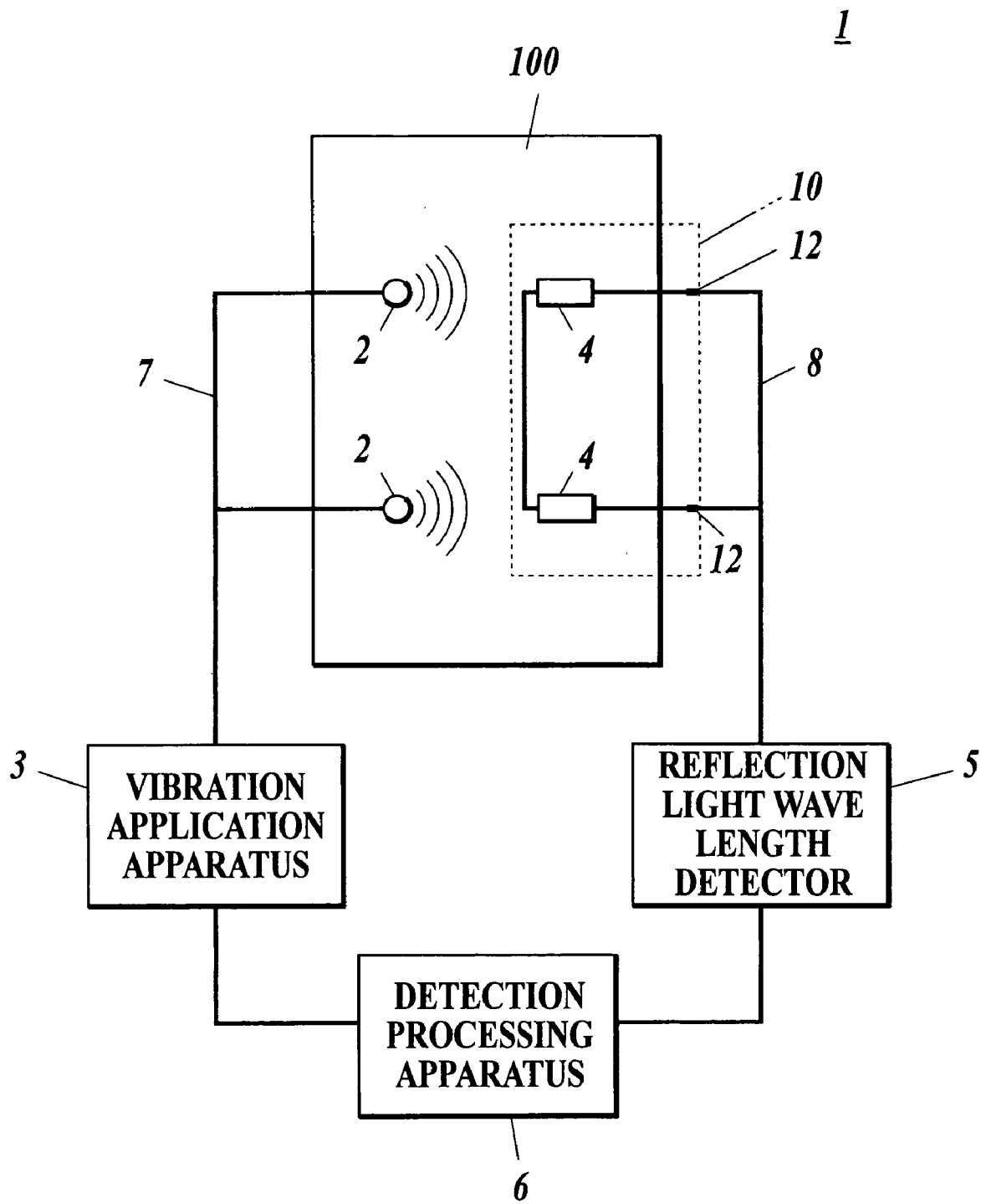
FIG. 1 is a block diagram to describe a functional structure of a damage detection system including a modular sensor for damage detection of a first embodiment of the present invention.

An embodiment of the present invention will be described with reference to figures.

First Embodiment

A first embodiment of the present invention will be described with reference to FIGS. 1 to 5. In this embodiment, described is an example where a modular sensor for damage detection is applied to a "damage detection system" that detects a damage of a composite material 100 for main wing of an aircraft, structured by bonding an outer plate 110, and a stringer 120 whose cross-section is a hat form, with a rivet 130 (refer to FIG. 2).

A structure of damage detection system 1 is described with reference to FIGS. 1 and 2.

As shown in FIGS. 1 and 2, the damage detection system 1 is structured with a plurality of piezo actuator 2 that are adhered to a planer surface of the composite material 100, a vibration application apparatus 3 that activates each piazo actuator by applying voltage, a plurality of FBG sensors 4 that are embedded into the composite material 100, a reflection light wave length detector 5 to detect change in characteristics of reflection light obtained from each of the FBG sensors 4, a detection processing apparatus 6 to determine whether damage exists or not based on outputs from the piezo actuator 2 and the reflection light wave length detector 5, and the like. As shown in FIG. 1, the damage detection system 1 is embedded with a modular sensor for damage detection 10 structured with FBG sensor 4 and the like. Description on the modular sensor for damage detection 10 will be given after.

As shown in FIG. 2, each of the piezo actuator 2 are adhered to the composite material 100 in the planar vicinity of points where detection of damage should be performed, and are electrically connected to the vibration application apparatus 3 through a wiring 7, as shown in FIG. 1. Each of the piezo actuator 2 has a characteristic that when a driving voltage is applied from outside, thickness of the piezo actuator 2 is changed in a thickness direction.

The vibration application apparatus 3 functions so as to apply instantaneous vibration to the composite material 100, by actuating specific piezo actuator 2, applying a driving pulse voltage to the specific piezo actuator 2 specified by the detection processing apparatus 6.

The FBG sensor 4 is provided on an optical fiber 11 which structures the modular sensor for damage detection 10 (shown in FIG. 2), and is structured by a core portion and a grating portion (a portion formed so that refractive index of the core portion is periodically changed) provided in this core portion. The grating portion of the FBG sensor 4 selectively reflects only a light of a particular wave length (Bragg wave length). As shown in FIG. 1, the FBG sensor 4 is connected to reflection light wave length detector 5 through a connector 12 and a wiring 8.

When vibration is applied to the FBG sensor 4, Bragg wave length is shifted in accordance with the distortion of the FBG sensor 4. For example, when vibration from a vibration source is transmitted to the FBG sensor 4 well, the FBG sensor 4 is largely distorted, and amount of wave length shift of the Bragg wave length becomes large. When vibration from the vibration source to the FBG sensor 4 is not transmitted well due to damage and the like, the FBG sensor 4 is distorted a little, and the amount of wave length shift of the Bragg wave length becomes small. By utilizing these properties, damage of the composite material 100 can be detected.

The reflection light wave length detector 5 irradiates the core portion of the FBG sensor 4 with an irradiation light from a predetermined light source, and calculates the amount of wave length shift by detecting light intensity distribution in a predetermined wavelength bandwidth of reflection light reflected by the FBG sensor 4. The amount of wave length shift calculated by the reflection light wave length detector 5 is outputted to the detection processing apparatus 6 and is used to detect damage.

The detection processing apparatus 6 is provided with a CPU which performs arithmetic processing in accordance with predetermined programs, a ROM which stores programs for various kinds of processing and controlling, a RAM which functions as a work area where data and the like are temporarily stored during the various kinds of processing, a monitor to display detection results as an image, and a data bus through which various instructions and data are transmitted among aforementioned units.

Within controlling the vibration application apparatus 3 by executing a predetermined program stored in the ROM, the CPU of the detection processing apparatus 6 applies vibration to the composite material 100 by actuating the specific piezo actuator 2 adhered on the composite material 100. In addition, within controlling the reflection light wave length detector 5 by executing a predetermined program stored in the ROM, the CPU of the detection processing apparatus 6 detects whether there is a damage or not in the composite material 100 according to the amount of wave length shift of the reflection light detected by the FBG sensor 4.

Next, a structure of modular sensor for damage detection 10 of the present embodiment is described with reference to FIGS. 2 and 3.

As shown in FIGS. 2 and 3, the modular sensor for damage detection 10 is structured with an optical fiber 11 provided with two FBG sensors 4, a connector 12 attached to an end portion of the optical fiber 11, a polyimide film 13 attached to the optical fiber 11 by a portion near the FBG sensor 4, and the like.

The optical fiber 11 is structured with a glass fiber including a core portion and a clad portion, and a heat resistant cover layer to cover the glass fiber. In the present embodiment, the optical fiber 11 of a thin diameter with an outer diameter of 52 μm (clad wire diameter 40 μm) is adopted, and a polyimide resin layer is used as the heat resistant cover layer. The optical fiber 11 is connected to reflection light wave length detector 5 through a connector 12 and a wiring 8 (refer to FIG. 1).

The connector 12 connects the wiring 8 connected to the reflection light wave length detector 5 and the optical fiber 11, and also contributes to improving visibility of the modular sensor for damage detection 10, thus functions to improve the manageability of module for damage detection. In the present embodiment, as a connector 12, adopted is a ferrule made of zirconia, which is significantly light and heat resistant, within a size corresponding to a wire diameter of the optical fiber 11 (outer diameter of 1.25 mm and inner diameter of 40 μm). Since the connector 12 is structured with a heat resistance material that can tolerate heat applied during hot forming of the composite material 100, the connector 12 can be embedded into a prepreg structuring the composite material 100, and can function without any problem even after being applied high temperature and high pressure during the hot forming.

In this embodiment, since the optical fiber 11 with thin diameter (outer diameter of 52 μm) is adopted, breakage of the optical fiber 11 is possible if stress is concentrated to the optical fiber 11 at a bonding portion of the optical fiber 11 and the connector 12. Therefore, as shown in FIG. 3, a reinforcing tube (polyimide tube) 14 with an outer diameter of 0.9 mm is provided at the bonding portion of the optical fiber 11 and the connector 12.

As shown in FIG. 3, the polyimide film 13 is structured hexagonally, and gradually narrows in width from center portion towards a boundary with the optical fiber 11, and functions so as to contribute to improving visibility of the modular sensor for damage detection 10, as well as manageability of modular sensor for damage detection 10. In addition, the polyimide film 13 is placed in a position with a regular interval from the FBG sensor 4. Therefore, a position of the FBG sensor can be easily grasped according to a position of the polyimide film 13.

In addition, since the polyimide film 13 has heat resistance to tolerate heat applied during hot forming of the composite material 100, the polyimide film 13 can be embedded into a prepreg structuring the composite material 100 or a fiber fabric. An area of the polyimide film 13 can be arbitrarily set according to a size of the structural composite material embedded with the modular sensor for damage detection 10. In addition, number of polyimide film 13 can be arbitrarily decided based on a number of end portion of the composite material 100 embedded with the modular sensor for damage detection 10.

Next, a method to manufacture a modular sensor for damage detection 10 of the present embodiment is described with reference to FIG. 4.

Figure 4A:
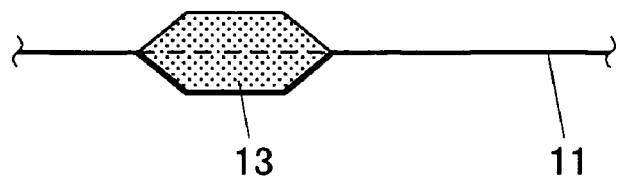
FIG. 4 is an explanatory view to describe a method to manufacture the modular sensor for damage detection of the first embodiment of the present invention.

First, the optical fiber 11 with an outer diameter of 52 μm and a pair of polyimide film 13 with a thickness of 25 μm, applied with an adhesive, is prepared. The pair of polyimide film 13 is attached so that it sandwiches the optical fiber 11 in between, thus the polyimide film 13 is attached to the optical fiber 11 (film attaching step). Next, margin of the polyimide film 13 is cut off so as the planer shape is shaped hexagonal as shown in FIG. 4A (film shape adjusting step).

Figure 4B:
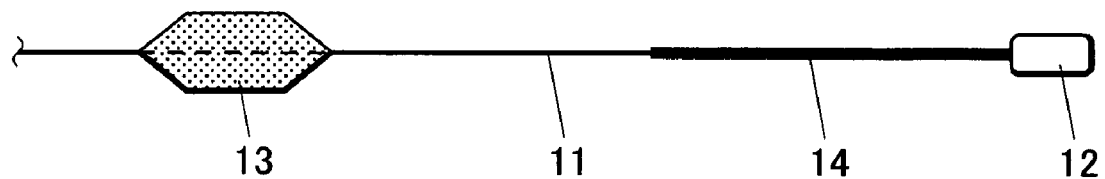

As shown in FIG. 4, after an end portion of the optical fiber 11 (portion where it has a predetermined interval from the end portion) is covered by the reinforcing tube 14 with a predetermined length for protection, the connector 12 is fixed to the end portion of the optical fiber 11 by an adhesive (connector fixing step). In the connector fixing step, an axis of the optical fiber 11 and an axis of the connector 12 is aligned so as to prevent loss of light at the connector 12. Within these steps, the modular sensor for damage detection 10 is obtained.

Next, steps involved when embedding a modular sensor for damage detection 10 of the present embodiment into the composite material 100 for a main wing of an aircraft is described with reference to FIGS. 2 and 5.

As shown in FIG. 2, the composite material 100 for a main wing of an aircraft is structured by bonding an outer plate 110 and a stringer 120 with a rivet 130, and in this embodiment, the modular sensor for damage detection 10 is embedded in a vicinity of the bonding surface of the outer plate 110 and the stringer 120, where damage occurs frequently.

Steps involved when embedding a modular sensor for damage detection 10 into the vicinity of the bonding surface of the outer plate 110 is described. When a plurality of prepregs (thickness of approximately 125 μm) is laminated to form the outer plate 110, the optical fiber 11 (including the FBG sensor 4) of the modular sensor for damage detection 10 and a part of the polyimide film 13 are sandwiched by the prepregs, then heat and pressure is applied to cure form the outer plate 110. On the contrary, when RTM (Resin Transfer Molding) method is adopted to form the outer plate 110, the optical fiber 11 (including the FBG sensor 4) of the modular sensor for damage detection 10 and a part of the polyimide film 13 are embedded into a fiber fabric to form outer plate, and then the fiber fabric is impregnated with a resin and applied with heat and pressure to cure form the outer plate 110.

Steps similar to aforementioned steps can be taken when embedding the modular sensor for damage detection into the vicinity of the bonding surface of the stringer 120. When a plurality of prepregs is laminated to form the stringer 120, the optical fiber 11 of the modular sensor for damage detection 10 and a part of the polyimide film 13 are sandwiched by the prepregs, then heat and pressure is applied to cure form the stringer 120. On the contrary, when RTM method is adopted to form the stringer 120, the optical fiber 11 of the modular sensor for damage detection 10 and a part of the polyimide film 13 are embedded into a fiber fabric to form a stringer, and then the fiber fabric is impregnated with a resin and applied with heat and pressure to cure form the stringer 120.

Figure 5A:
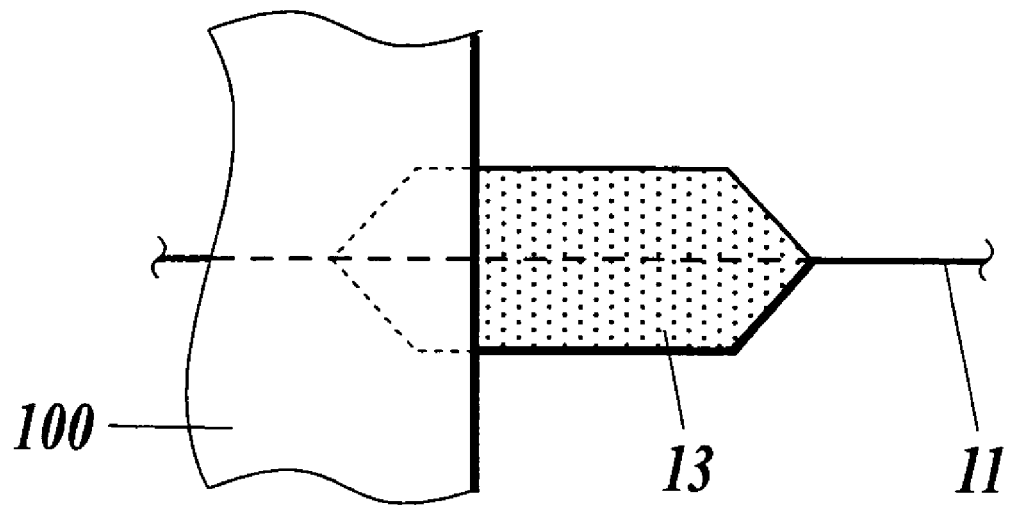
FIG. 5 is a view showing a polyimide film of the modular sensor for damage detection of the first embodiment of the present invention, being placed at an end portion of the composite material, wherein A is a plane view and B is a side view.
Figure 5B:
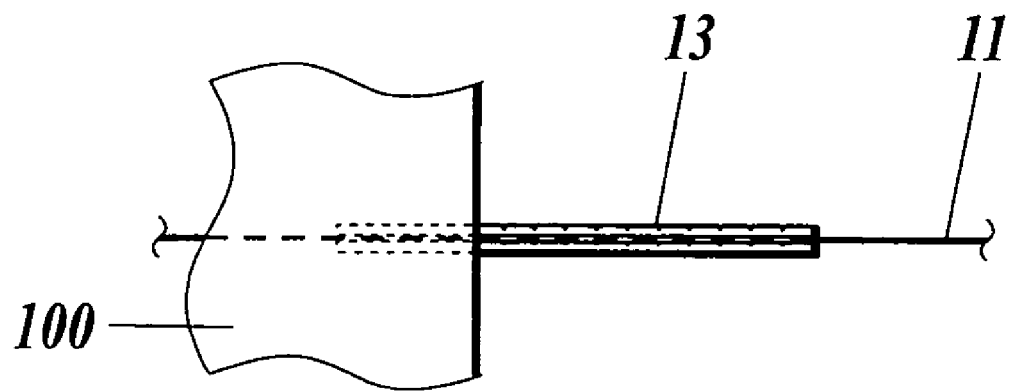

In addition, as shown in FIGS. 2 and 5, when embedding the modular sensor for damage detection 10 into the outer plate 110 or the stringer 120, a center portion of the polyimide film 13 (broad portion) is placed on the end portion of the outer plate 110 or the stringer 120. Since the polyimide film 13 is broad in the center portion and has high strength and stiffness, by placing this center portion at the end portion of the outer plate 110 or the stringer 120, the optical fiber 11 of thin diameter can be avoided from being bent steeply at the end of the composite material, thus concentration of stress can be prevented.

The modular sensor for damage detection 10 as described in the present embodiment has the connector 12 connected at the end portion of the optical fiber 11, and is structured by fixing a part of the polyimide film 13 to the optical fiber 11. Therefore, the modular sensor for damage detection 10 has a high level of visibility compared to optical fiber alone, achieving benefit of significant manageability. In addition, by placing the polyimide film 13 at the end portion of the outer plate 110 or the stringer 120 when embedding the modular sensor for damage detection 10 into the composite material 100, breakage of the optical fiber 11 can be prevented by inhibiting stress concentration to the optical fiber 11.

In the described modular sensor for damage detection 10 of the present embodiment, since an interval between the FBG sensor 4 and the polyimide film 13 is constant, it is easy to grasp a position of the FBG sensor 4 according to a position of the polyimide film 13. Therefore, the FBG sensor 4 can be placed at precise position, and degree of detection accuracy is improved.

Since the described polyimide film 13 structuring the modular sensor for damage detection 10 of the present embodiment is heat resistant, hot forming can be performed to the composite material 100 (outer plate 110 and stringer 120) with the polyimide film 13 partly embedded.

Since the described polyimide film 13 structuring the modular sensor for damage detection 10 of the present embodiment is structured so that the film gradually narrows down in width from center portion towards the boundary with the optical fiber 11 (the film gradually increases in width from the boundary with the optical fiber 11 towards center portion), the center portion has the highest strength and stiffness. Therefore, by placing the center portion of the polyimide film 13 on an end portion of the outer plate 110 or the stringer 120 when embedding the modular sensor for damage detection 10 into the composite material 100, breakage of the optical fiber 11 can be effectively prevented. In addition, since the polyimide film 13 is structured so as to gradually narrow in width from center portion towards the boundary with the optical fiber 11, the stiffness decreases gradually from the center portion towards the boundary with the optical fiber 11. Therefore, flexibility when embedding into the composite material 100 is high.

Since the described modular sensor for damage detection 10 of the present embodiment uses optical fiber 11 of thin diameter, and the outer diameter of the optical fiber 11 (52 µm) is set to be less than the thickness of one prepreg layer (approximately 125 µm), strength degradation of the composite material 100 when modular sensor for damage detection 10 is embedded can be prevented.

Since the described modular sensor for damage detection 10 of the present embodiment is reinforced by the reinforcing tube 14 at bonded portion of the optical fiber 11 and connector 12, breakage of the optical fiber 11 can be suppressed or prevented by preventing concentration of stress to the optical fiber 11 when connecting connector to a predetermined adaptor.

Since the described connector 12 of the modular sensor for damage detection 10 of the present embodiment is structured with a heat resistance material, hot forming can be performed with the modular sensor for damage detection 10 embedded into the composite material 100. In addition, since the connector is significantly light and small, breakage of the optical fiber 11 due to own weight of connector 12 can be prevented.

Since the described composite material 100 of the present embodiment has the FBG sensor 4 of the modular sensor for damage detection 10 embedded, by adopting damage detection system 1 including this FBG sensor 4, damage can be detected with high accuracy. Therefore, by adopting the composite material of the present embodiment, "damage tolerance design", which can take the properties of the composite material (light and high in strength) fully in advantage, is be achieved, enabling realization of drastic weight decrease of a structure (main wing of an aircraft).

In the present embodiment, example with the planer shape of the polyimide film 13 being shaped hexagonal has been described, however, other shapes (rhombus shape for example) structured so as the film gradually narrows in width from center portion towards a boundary with the optical fiber 11 can be adopted.

Second Embodiment

Next, description of a second embodiment of the present invention will be described with reference to FIGS. 6 and 7.

A modular sensor for damage detection 10A of the present embodiment is a modification of the modular sensor for damage detection 10 of the first embodiment, in that polyimide tube 15 is used in place of the polyimide film 13, and other structures are practically the same with the first embodiment. Therefore, description will be given only for the modified structure, and numeric reference identical to that of the first embodiment is applied for the same structure with the first embodiment. In addition, since a damage detection system 1 embedded with the modular sensor for damage detection 10A of the present embodiment is practically the same with the damage detection system 1 of the first embodiment, description will be omitted.

Figure 6:
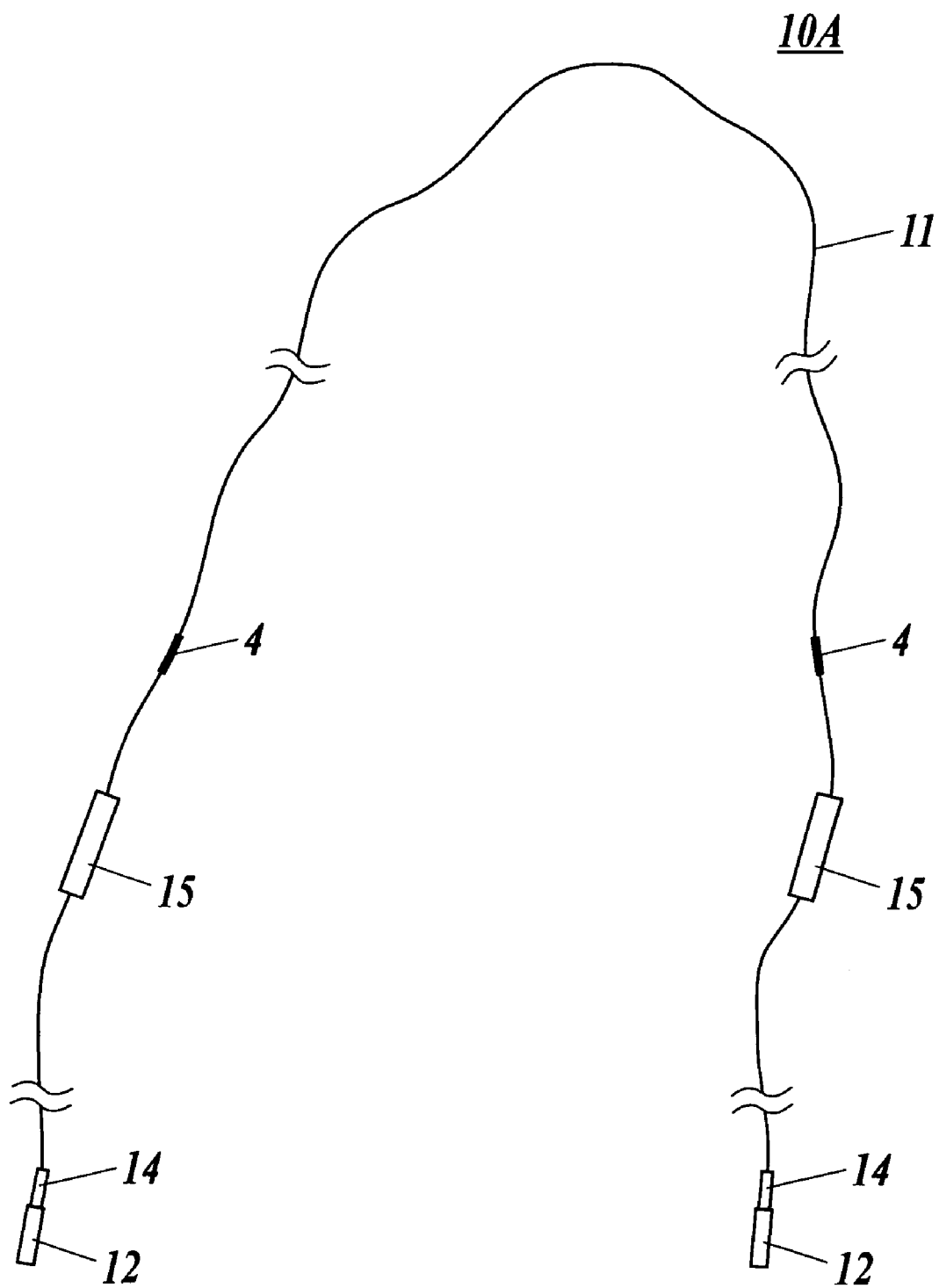
FIG. 6 is a conceptual diagram of the modular sensor for damage detection of a second embodiment of the present invention.

As shown in FIG. 6, the modular sensor for damage detection 10A of the present embodiment is structured with a optical fiber 11 provided with an FBG sensor 4, a connector 12 connected to an end portion of the optical fiber 11, a polyimide tube 15 which partly covers the optical fiber 11, and the like.

Figure 7:
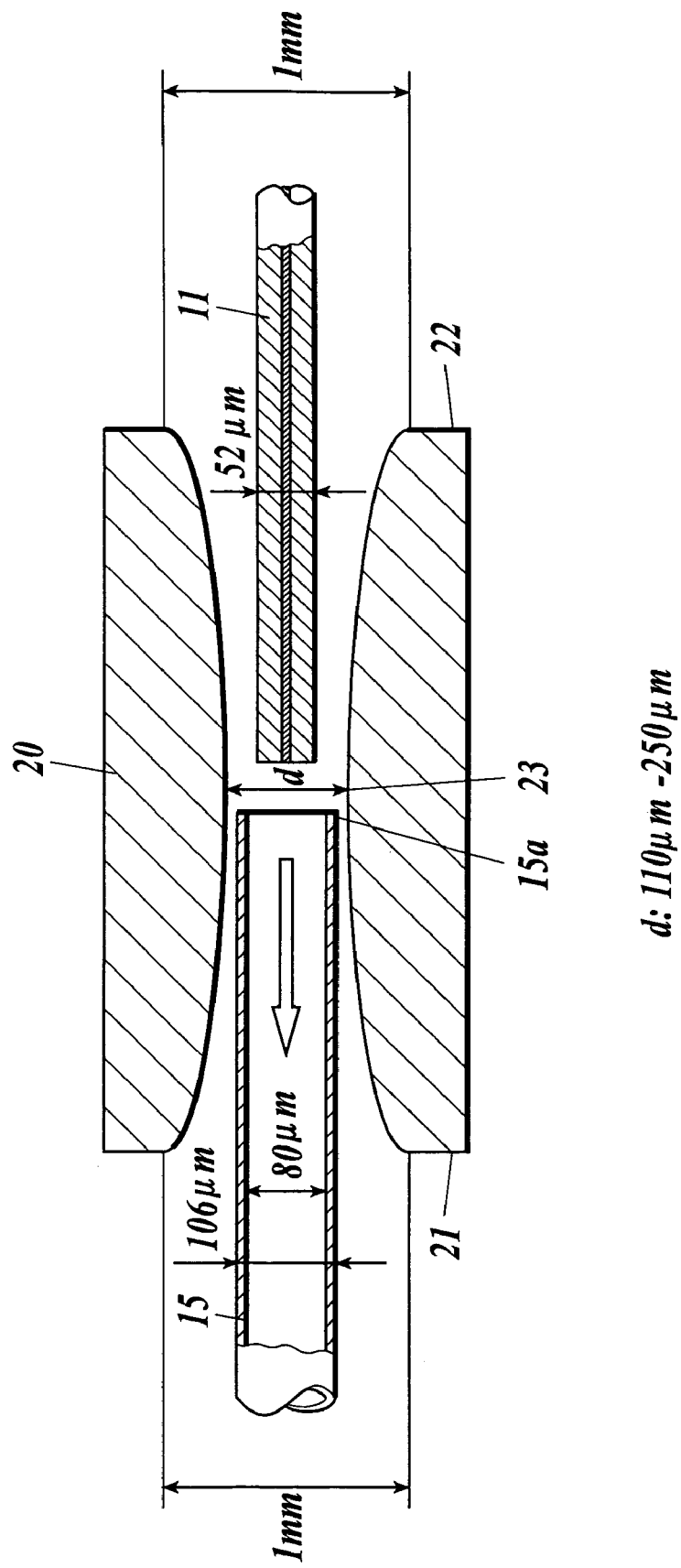
FIG. 7 is an explanatory view to describe a method to manufacture the modular sensor for damage detection of the second embodiment of the present invention.

As shown in FIG. 7, the polyimide tube 15 has an outer diameter (approximately 100 µm) larger than an outer diameter of the optical fiber 11 (52 µm), which contributes to improvement in visibility of the modular sensor for damage detection 10A, and functions so as to improve the manageability of the modular sensor for damage detection 10A. In addition, since the polyimide tube 15 has an inner diameter (80 µm) larger than the outer diameter of the optical fiber 11 (52 µm), the optical fiber 11 can be inserted and moved in the polyimide tube 15. That is, the polyimide tube 15 is movable with respect to the optical fiber 11.

Since the polyimide tube 15 has heat resistance property to tolerate heat applied when composite material is under hot forming, the polyimide tube 15 can be embedded into components of the composite material such prepreg and fiber fabric. Length of the polyimide tube 15 can be arbitrarily set according to length of the optical fiber 11, or size and shape of the structural composite material in which the modular sensor for damage detection 10A is embedded. In addition, number of the polyimide tube 15 can be arbitrarily set according to number of the FBG sensor 4, or number of end portion of the structural composite material in which the modular sensor for damage detection 10A is embedded.

Next, a method to manufacture the modular sensor for damage detection 10A of the present embodiment is described.

First, an optical fiber 11 with an outer diameter of 52 µm and a polyimide tube 15 with an outer diameter of 106 µm and an inner diameter of 80 µm is prepared. As shown in FIG. 7, a glass capillary 20 (tubular member), provided with a inner diameter which is slightly larger at a center portion 23 and fully larger at both ends 21 and 22 than the outer diameter of the polyimide tube 15 (106 µm) and increases gradually from the center portion 23 to both ends 21 and 22 of the tubular member, is prepared (tubular member preparing step). Size of the inner diameter at the center portion 23 of the glass capillary 20 is set to be larger than the outer diameter of the polyimide tube 15 (106 µm), and within the size capable to restrict the movement of the polyimide tube 15 in the diameter direction (110 to 250 µm for example). Size of the diameter at the both ends 21 and 22 of the glass capillary 20 is set so that the optical fiber 11 or the polyimide tube 15 can be easily inserted (1 mm for example).

Next, as shown in FIG. 7, through one end 21 of the glass capillary 20, is inserted one end portion 15A of the polyimide tube 15, and by placing this end portion 15A in the vicinity of the center portion 23 with a smallest inner diameter, movement of the polyimide tube 15 in the diameter direction can be restricted (tube insertion step). In addition, through the other end 22 of the glass capillary 20, is inserted the optical fiber 11, simultaneously inserting the optical fiber 11 into the end portion 15A of the polyimide tube 15 (optical fiber insertion step). Then the glass capillary 20 is removed from a polyimide tube side (tubular member removal step). The optical fiber 11 inserted into the polyimide tube 15 is movable within the polyimide tube 15.

Next, as shown in FIG. 6, after an end portion of the optical fiber 11 (portion where it has a predetermined interval from the end portion) is covered by the tube 14 with a predetermined length for protection, the connector 12 is fixed to the end portion of the optical fiber 11 by an adhesive (connector fixing step). In the connector fixing step, an axis of the optical fiber 11 and an axis of the connector 12 is aligned so as to prevent loss of light at the connector 12. Within these steps, the modular sensor for damage detection 10A is obtained.

The modular sensor for damage detection 10A as described in the present embodiment has the connector 12 connected at the end portion of the optical fiber 11, and is structured by covering a part of the optical fiber 11 with the polyimide tube 15. Therefore, the modular sensor for damage detection 10 has a high level of visibility compared to optical fiber alone, achieving benefit of significant manageability. In addition, by placing the polyimide tube 15 at the end portion of the structural composite material when embedding the modular sensor for damage detection 10A into the structural composite material, breakage of the optical fiber 11 can be prevented by inhibiting stress concentration to the optical fiber 11.

Since the polyimide tube 15 of the modular sensor for damage detection 10A as described in the present embodiment is movable with respect to the optical fiber 11, the polyimide tube 15 can be moved according to the position of an end portion of the structural composite material. Therefore, the modular sensor for damage detection 10A of the present embodiment can be applied to structural composite material with various shapes.

Since the polyimide tube 15 of the modular sensor for damage detection 10A as described in the present embodiment has heat resistance, hot forming of composite material can be conducted with a part of this polyimide tube 15 embedded.

Since the described manufacturing method of the modular sensor for damage detection 10A in the present embodiment includes adopting a specific tubular member (glass capillary 20) which has a widened inner diameter at the both ends 21 and 22 for easy insertion of the polyimide tube 15 or the optical fiber 11, as well as restricting the movement of the end portion 15A of the polyimide tube 15 in the diameter direction, inserting the optical fiber 11 into the polyimide tube 15 becomes significantly easy. Therefore, the modular sensor for damage detection 10A can be manufactured in short time efficiently.

Figure 8:
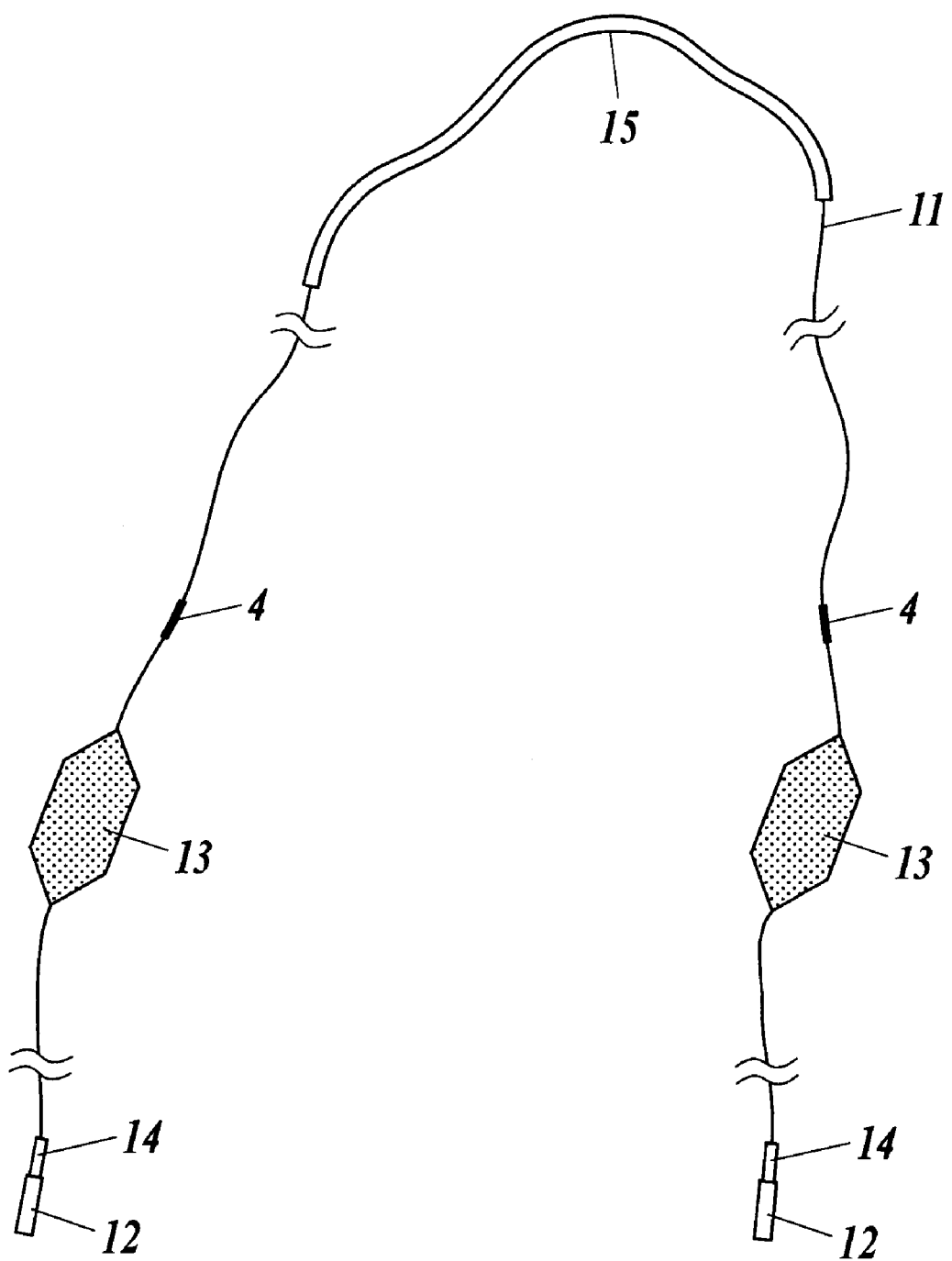
FIG. 8 is a conceptual diagram of the modular sensor for damage detection of a third embodiment of the present invention.

In the present embodiment, examples where polyimide film 13 was applied to the optical fiber 11, and polyimide tube 15 was applied to the optical fiber 11 was described. However, as shown in FIG. 8, modular sensor for damage detection can be structured with both the polyimide film 13 and the polyimide tube 15 applied to the optical fiber 11 (third embodiment).

In the present embodiment, example where an optical fiber with a thin diameter (outer diameter of 52 μm) was described. However, an optical fiber with a normal diameter (outer diameter of 125 μm to 145 μm) can be used. In addition, by connecting an optical fiber with a thin diameter and an optical fiber with a normal diameter, visibility and manageability can somewhat be improved.

In the present embodiment, example where tube and film made of polyimide was used as tube and film to structure the modular sensor for damage detection was described. However, tube and film structured by other heat resistant material can be used.

In the present embodiment, as an example of a structural composite material, a composite material 100 for main wing of an aircraft, structured with an outer plate 110 and a stringer 120 with a hat form was described. However, other structural composite material can be applied with the present invention as a matter of course.

The entire disclosure of Japanese Patent Application No. Tokugan 2004-362867 filed on Dec. 15, 2004 including specification, claims, drawings and summary are incorporated herein by reference in its entirety.

What is claimed is:

1. A modular sensor for damage detection comprising:
an optical fiber including an FBG sensor;
two connectors connected to both end portions of the optical fiber;
two reinforcing tubes to cover both end portions of the optical fiber, and
a tube to partly cover the optical fiber,
wherein the optical fiber movably penetrates the tube and the tube is movable between the two reinforcing tubes.

2. The modular sensor for damage detection as claimed in claim 1, wherein the tube comprises a heat resistant material.

3. The modular sensor for damage detection as claimed in claim 1, further comprising a film covering a portion of the optical fiber.

4. The modular sensor for damage detection as claimed in claim 1, wherein said reinforcing tubes reinforce connecting portions of the optical fiber and the connectors.

5. A manufacturing method for manufacturing a modular sensor for damage detection, comprising:
a tubular member preparing step to prepare a tubular member, provided with an inner diameter which is slightly larger at a center portion and fully larger at both ends than an outer diameter of a tube and which inner diameter increases gradually from the center portion of said tubular member to both ends of the tubular member;
a tube insertion step to insert one end portion of the tube into the tubular member through a first end of the tubular member and restrict a movement of the tube in a diameter direction by placing the end portion in a vicinity of the center portion;
an optical fiber insertion step to insert an optical fiber into the tubular member through a second end of the tubular member, and then into the end portion of the tube;
a tubular member removal step to remove the tubular member from the tube and the optical fiber; and
a connector fixing step to fix the connector to an end portion of the optical fiber.

6. A structural composite material embedded with the FBG sensor of the modular sensor for damage detection as claimed in claim 1.

7. The structural composite material embedded with the modular sensor for damage detection as claimed in claim 1, wherein the FBG sensor is embedded into a stress concentrating portion of the structural composite material, without being covered with the tube, and the tube is partly embedded into an end portion of the structural composite material.

8. The modular sensor for damage detection as claimed in claim 1, wherein the connectors are configured to connect the optical fiber to a reflection light wave length detector through wires.

9. The modular sensor for damage detection as claimed in claim 1, wherein the connectors are zirconia ferrules.

10. The modular sensor for damage detection as claimed in claim 1, wherein the reinforcing tubes are polyimide tubes.

11. The modular sensor for damage detection as claimed in claim 1, further comprising two films covering portions of the optical fiber, wherein the tube is movable between the films.

12. A modular sensor for damage detection comprising:
an optical fiber including a FBG sensor; and
a film covering a portion of the optical fiber,
wherein the film is arranged in a position at a distance from the FBG sensor and is structured so that the film gradually narrows in width from a center portion of the film towards both boundaries with the optical fiber.

13. The modular sensor for damage detection as claimed in claim 12, wherein the film comprises a heat resistant material.

14. The modular sensor for damage detection as claimed in claim 12, further comprising a reinforcing tube to reinforce a bonding portion of the optical fiber and the connector.

15. The modular sensor for damage detection as claimed in claim 14, wherein the reinforcing tube is a polyimide tube.

16. A structural composite material embedded with the FBG sensor of the modular sensor for damage detection as claimed in claim 12.

17. The structural composite material embedded with the modular sensor for damage detection as claimed in claim 12, wherein the FBG sensor is embedded into a stress concentrating portion of the structural composite material, and the film is partly embedded into an end portion of the structural composite material.

18. The modular sensor for damage detection as claimed in claim 12, further comprising a connector connected to an end portion of the optical fiber.

19. The modular sensor for damage detection as claimed in claim 18, wherein the connector is configured to connect the optical fiber to a reflection light wave length detector through a wire.

20. The modular sensor for damage detection as claimed in claim 18, wherein the connector is a zirconia ferrule.

21. The modular sensor for damage detection as claimed in claim 12, further comprising a tube to partly cover the optical fiber, wherein the tube is movable with respect to the film.

22. A manufacturing method for manufacturing a structural composite material for damage detection, comprising:
a connecting step for connecting a connector to an optical fiber including an FBG sensor, wherein said connector is made of a heat resistant material which tolerates heat applied when the structural composite material which a modular sensor including the connector and the optical fiber embedded therein is under hot forming;
an embedding step for embedding the modular sensor into the structural composite material;
and a hot forming step for forming the composite material with heat and pressure after the connecting step.

23. The manufacturing method for manufacturing a structural composite material for damage detection as claimed in claim 22, further comprising:
a providing step for providing a reinforcing tube at a bonding portions of the optical fiber and the connector, and performing said providing step before the hot forming step.

24. The manufacturing method for manufacturing a structural composite material for damage detection as claimed in claim 23, wherein the reinforcing tube is a polyimide tube.

25. The manufacturing method for manufacturing a structural composite material for damage detection as claimed in claim 22, further comprising,
a film attaching step for attaching a pair of films such that said pair of films forms a sandwich with the optical fiber including the FBG sensor, and
a film shape adjusting step for adjusting such that the film is structured so that the film gradually narrows in width from a center portion of the film towards a boundary with the optical fiber.

* * * * *